United States Patent [19]

Pellerin et al.

[11] Patent Number: 4,838,085

[45] Date of Patent: Jun. 13, 1989

[54] METHODS AND APPARTAUS FOR NON-DESTRUCTING EVALUATION OF THE MECHANICAL PROPERTIES OF COMPOSITE MATERIALS

[75] Inventors: Roy F. Pellerin; Robert J. Ross, both of Pullman, Wash.

[73] Assignee: Washington State University Research Foundation, Inc., Pullman, Wash.

[21] Appl. No.: 843,717

[22] Filed: Mar. 25, 1986

[51] Int. Cl.$^4$ .......................................... G01N 29/00
[52] U.S. Cl. ..................................................... 73/597
[58] Field of Search ................. 73/597, 588, 584, 582, 73/574

[56] References Cited

U.S. PATENT DOCUMENTS

| | | | |
|---|---|---|---|
| 2,439,130 | 4/1948 | Firestone | 73/597 |
| 3,087,138 | 4/1963 | Toulis | 73/597 |
| 3,423,991 | 7/1969 | Collins | 73/600 |
| 3,504,532 | 4/1970 | Muenow et al. | 73/597 |
| 3,512,400 | 5/1970 | Lynnworth | 73/597 |
| 3,513,690 | 5/1970 | Pellerin et al. | 73/594 |
| 3,858,437 | 7/1975 | Jarzynski et al. | 73/599 |
| 3,861,200 | 7/1975 | Dory | 73/599 |
| 3,888,108 | 6/1975 | Brands | 73/12 |
| 4,147,064 | 4/1979 | Bond | 73/597 |
| 4,163,393 | 8/1979 | Gutierrez et al. | 73/584 |
| 4,201,093 | 5/1980 | Logan | 73/609 |
| 4,338,820 | 7/1982 | Jassby | 73/597 |
| 4,361,154 | 11/1982 | Pratt, Jr. | 128/660 |
| 4,420,210 | 9/1983 | Vandeberg | 73/12 |
| 4,481,820 | 11/1984 | Thomann | 73/597 |
| 4,492,117 | 7/1985 | Chubachi | 73/597 |

FOREIGN PATENT DOCUMENTS 918286 of 1973 Canada .

OTHER PUBLICATIONS

"The Acoustic Impact Technique", R. Schoeer, Non-Destructive Testing, Jun. 1970, vol. 3, No.3.
"Promising Quantitative NDE Techniques for Composite Materials", J. H. Williams, Jr. et al., Mat. Eval./4-3/Apr. '85.
"Ultrasonic Inspection of Carbon-Epoxy Composites", D. J. Hagemaier et al., Mat. Eval./43/Apr. 85, ASNDT.
J. H. Kaiserlik, "Attenuation of LSW as Indicator of Lumber Streght", Washington State University 1975.
J. H. Kaiserlik et al, "SW Attenuation as an Indicator of Lumber Strength", Forest Products Journal, vol. 27, No. 6, Jun. '76.
Autom. & Simultaneous Measurm. of Ultrasonic Velocity and Attenuation Changes, Matsuda et al, Rev. Sci. Inst. 50(10), Oct. 1979.
Ultrasonic Wave Propagation Principles in Composite Mat. Insp. J. L. Rose, Materials Evaluation/43/Apr. 1985, ASNDT.
Joseph Henry Kaiserlik, "Attenuation of Longitudinal Stress Waves as an Indicator of Lumber Strength", Washington State University, 1975.
J. H. Kaiserlik & R. F. Pellerin, "Stress Wave Attenuation as an Indicator of Lumber Strength", *Forest Products Journal*, vol. 27, No. 6, pp. 39–43.

Primary Examiner—Stewart J. Levy
Assistant Examiner—Louis M. Arana
Attorney, Agent, or Firm—Wells, St. John & Roberts

[57] ABSTRACT

Methods and apparatuses for non-destructively testing and evaluating mechanical properties of composite materials such as particleboard, plywood, graphic fiber-epoxy composites and other bonded composite materials. The composite material structural elements are subjected to an impact, force or other stress wave producing stimulus. The resulting stress wave is sensed at two different points in time. The speed and attenuaton rate of the stress wave are determined. Measurements of the composite material density are combined with the stress wave speed and attenuation rate into an equation also defined by predetermined experimentally derived parameters. The experimentally derived parameters are specific to the test system, materials, and structural elements being tested. Apparatuses disclosed have sensors which are positioned to determine the stress wave intensity at spaced positions from the stress wave inducing device. The sensors can be retractably mounted and arranged in concentric circles. A singular magnetic sensor for repeatedly detecting a stress wave reflected within a bar or panel is also disclosed.

6 Claims, 4 Drawing Sheets

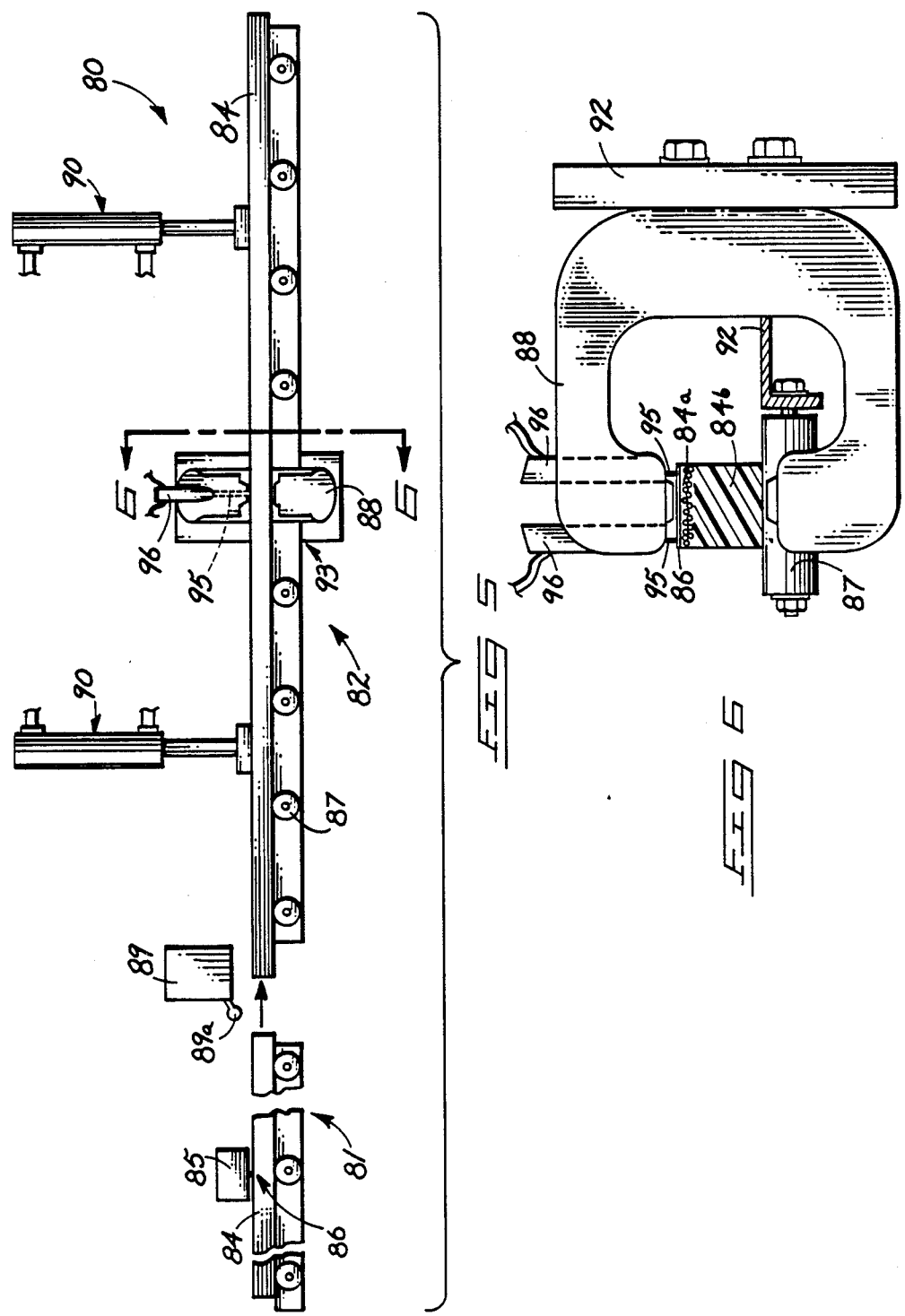

4,838,085

METHODS AND APPARTAUS FOR NON-DESTRUCTING EVALUATION OF THE MECHANICAL PROPERTIES OF COMPOSITE MATERIALS

TECHNICAL FIELD

The technical field of this invention includes methods and apparatus for non-destructively testing composite materials, such as particleboard, oriented strand board, wafferboard, medium density fiberboard, hardboard, insulation board, plywood, epoxy-graphite composites and other non-homogeneous composite materials.

BACKGROUND OF THE INVENTION

The development of improved composite materials has led to increased use of these materials in both engineering and non-engineering applications. Wood-based composite materials such as plywood, wafferboard, and oriented strand board are widely used as engineered structural components. Particleboard, medium density fiberboard, hardboard and other similar composites are typically used in non-engineering applications. Epoxy-graphite and other similar elongated fiber-matrix composites have found acceptance in aviation, sports products and in other applications where high strength and light weight are desired.

All materials have some variability in the strength capability of individual pieces which are similarly manufactured. However, this is a much greater problem with composite materials as compared to homogeneous engineering materials such as metals. Composite materials have relatively wide variations in strength due to the composite nature of the products and the difficulty in achieving uniform strength in the bonding used to join the components together. Variations in the feedstocks and other factors make manufacture of uniformly strong and elastic structures from composite elements difficult and costly.

Manufacturers of composite materials suffer significant quality control problems in connection with bonding and continuity of the components used to make up the composite. Epoxy-graphite fiber composites suffer failure at the fiber/matrix bond. Problems also occur with respect to fiber strength, breakage and orientation, all of which affect overall strength and elastic properties of the structural element. Composite materials also suffer common failures and reduced strength capabilities due to poor bonding, voids, cracks and other problems specific to individual pieces of the composite material.

Previously it has been impossible to nondestructively test structural elements made from composite materials to provide reliable indication of the strength properties of the particular element being tested. It has been typical to test a large number of specimens and to arrive at acceptable design loads based upon the performance exhibited by the vast majority of such samples and using appropriate factors of safety. Heretofore it has not been acceptable to use varying strength capabilities for various pieces because of the fact that the strength of each piece could not be accurately assessed without destructively testing.

In the particleboard, fiberboard, plywood, wafferboard and similar industries, there have been little or no way of assuring that individual members have the desired strength capabilities. Manufacturers have typically used non-strength indicators such as visual indentification of separations, cracks, pockets and other defects in order to selectively eliminate structurally insufficient pieces. Test pieces have also typically been removed at random for destructive testing to obtain a general measure of product strength capabilities. Such manufacturing techniques have not reliably indentified internal defects and have further led to significant waste of usable product, both through testing and removal of cosmetically defective but useful product. Accordingly, there has been a significant need for methods and apparatus for non-destructively testing structural elements made of composite materials to provide a reliable indication or prediction of the strength properties of each particular element.

U.S. Pat. No. 3,423,991 to Collins shows an apparatus for ultrasonically inspecting plywood panels for delaminations and other defects. The apparatus rollably imparts ultrasonic vibrations to the panels along one side and uses a sensing element on the opposite side. High rates of ultrasonic attenuation cause the sensor to have reduced reception thus indicating the location of defects. Reflected pulse-echo mode operation is also possible. The Collins' invention does not seek to predict mechanical properties of the plywood panels for engineering use, but instead is used to identify defective areas of the panels.

U.S. Pat. No. 3,888,108 to Brands shows a pavement testing apparatus adapted for use with conrete pavement. The apparatus uses a falling hammer to impart vibrations to the pavement. The intensity of the vibrations are sensed at two disparate points by accelerometers. The attenuation of the vibrations is used as an indicator of the structural integrity of the pavement.

U.S. Pat. No. 3,504,532 to Muenon shows a non-destructive testing system using vibrations perceived at two locations on the test specimen.

These and other prior art patents have not taught reliable methods or apparatuses for non-destructively testing structural elements made from composite materials in order to provide a usable indication of the strength and elastic properties of the individual items being tested.

BRIEF DESCRIPTION OF THE DRAWINGS

Preferred embodiments of the invention are shown in the accompanying drawings, in which:

FIG. 5 is a schematic side elevational view of a further embodiment of the invention;

FIG. 6 is an enlarged cross-sectional view taken along line 6—6 of FIG. 5; and

DETAILED DESCRIPTION OF THE PREFERRED EMBODIMENT

In compliance with the constitutional purpose of the Patent Laws "to promote the progress of science and useful arts" (Article 1, Section 8), applicant submits the following disclosure of the invention.

Figure 1:
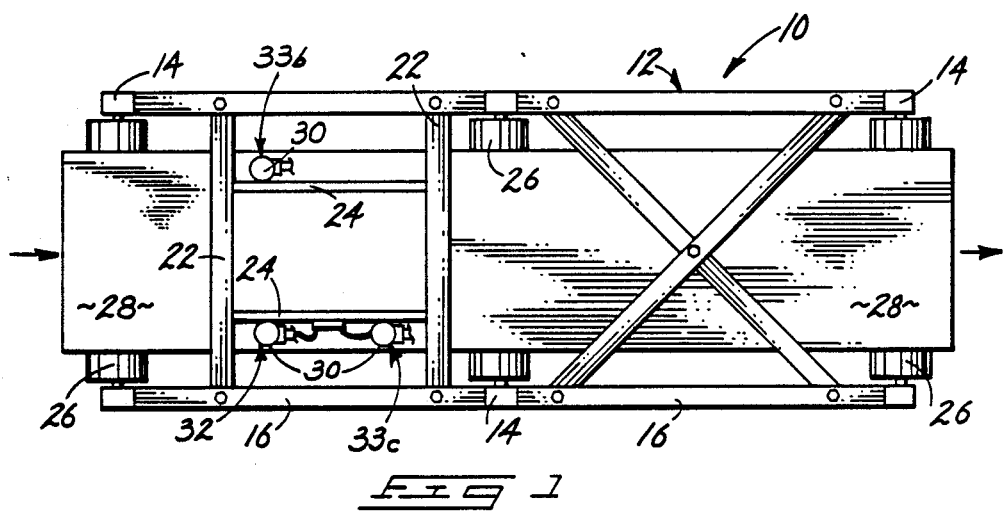
FIG. 1 is a top or plan view of a first embodiment of the invention.
Figure 2:
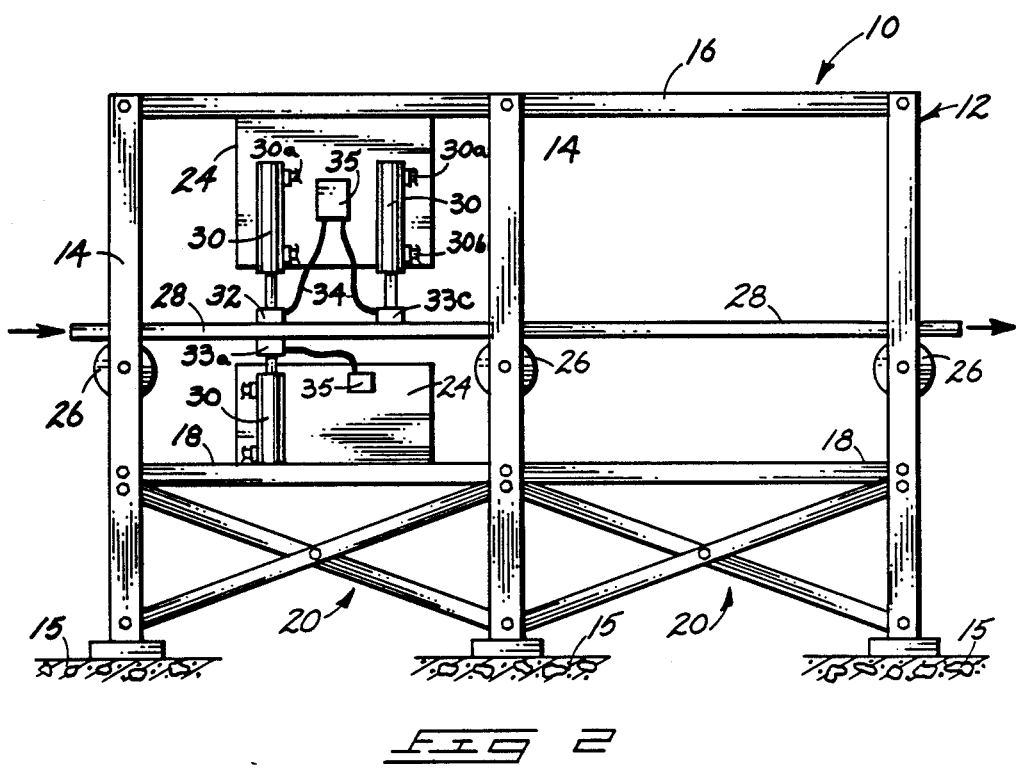
FIG. 2 is a side elevational view of the embodiment of FIG. 1.

A preferred form of apparatus for non-destructively testing, evaluating and predicting mechanical properties of composite structural elements is shown in FIGS. 1 and 2. The non-destructive testing apparatus 10 includes a structural framework 12 which can be of numerous suitable designs. FIGS. 1 and 2 show framework 12 including a plurality of upright columns 14 which are mounted to a foundation or other supporting structure 15. A plurality of upper rails 16 and lower rails 18 extend between and are connected to columns 14. Cross braces 20 are also advantageously included. Transverse beams 22 extend across testing machine 10 between rails 16 and 18 to support vertical mounting plates 24.

Framework 12 is further adapted to rotatably mount a plurality of panel support rollers 26. Rollers 26 are advantageously driven by motor means (not shown) which can be internal to the rollers or external and mechanically connected thereto using gears, belts or other suitable drives (not shown). Rollers 26 receive, support and advantageously convey panels 28 or other structural elements being tested by apparatus 10. Additional rollers 28 beyond the three shown are clearly possible for supporting panel 28.

Testing machine 10 further includes a plurality of pneumatic or hydraulic rams 30 which are connected to framework 12 such as at vertical mounting plates 24. Rams 30 are supplied via lines 30a and 30b to a suitable supply of pressurized fluid controlled in a typical manner. Rams 30 are used to movably mount one or more stress wave producing units 32. FIGS. 1 and 2 show a single stress wave producing unit 32. One or more receiver or sensor units 33 are also included and movably mounted on rams 30. Rams 30 are used to extend and retract units 32 and 33 from close proximity or contact with panel 28 depending on the specific type of units employed.

The exact configuration of stress wave producing unit 32 and sensor units 33 may vary depending upon the geometry of the panels or other specimens being evaluated and the accuracy of information desired. Stress wave unit 32 can be of any suitable type used to produce a freely propagating, longitudinal stress wave in panel 28. Stress wave unit 32 is advantageously adapted to mechanically impact panel 28 using a moving mass (not shown) and a motivating solenoid (not shown). Alternatively, stress wave producer 32 can be a piezoelectric impactor or stress applicator preferably designed to deliver single or multiple discrete impacts or forces to specimen panel 28 thereby inducing stress waves therein. Other impacting and stress wave producing units are also possible as will be apparent to those of skill in the art.

FIGS. 1 and 2 show a plurality of receiver or sensor units 33. Sensor units 33 are shown advantageously mounted at three locations. Sensor units 33 are shown adapted to engage panel 28 when placed into extended positions by rams 30. Rams 30 and sensor units 33 are retractable when contact is not desired such as when panel 28 is loaded and removed.

A first sensor unit 33a is preferably placed directly opposite from impactor 32 beneath panel 28. A second sensor 33b is preferably disposed transversely across panel 28. A third sensor 33c is advantageously placed longitudinally along panel 28 near the same side edge adjacent to impactor 32, and upon the same panel face surface. This configuration for units 32 and 33 allows longitudinal stress waves to pass through the thickness of the panel, transversely across the panel, and longitudinally along the panel prior to being detected by sensors 33. The disparate positions of sensors 33 cause any stress wave to be sensed at different times because of the different lengths of travel between the point of impact and the particular sensor in question.

Sensor units 33 can be of a variety of types which are capable of accurately measuring the time at which a stress wave passes the sensor, and the intensity of the stress wave as it so passes. Sensors 32 can be capable of measuring either displacement, velocity or acceleration since the amplitude or intensity of the stress wave can be derived from the relative displacement, velocity or acceleration as is well known in wave physics.

Stress wave sensors 33 can be static sensors adapted to contact or otherwise measure wave dynamics of the specimen. Alternatively, sensors 33 can be dynamic or rolling transducers as suggested by U.S. Pat. No. 3,423,991 to Collins. Such rolling transducers in the form of accelerometers are commercially available from companies such as Automation Industries, Inc., Sperry Products Division, Danbury, Conn., (their models sold under the trademark, Wheel Search Units).

A preferred sensor unit 33 is a contacting piezoelectric accelerometer well known in the art. Also useful are stress gages. Both of these sensor types are available from PCB Piezoelectronics of DePew, N.Y. Widely known strain gage sensors can also be used by affixing or securely engaging with the test specimen. Sensors 33 can also be non-contacting optical displacement followers which can use light reflective grids or coatings applied to the face of panel 28 at suitable points upstream from testing apparatus 10. Such optical displacement systems are manufactured by Optron Corp., Woodbridge, Conn.

Stress wave unit 32 and wave sensors 33 are electrically connected via cables 34 to electrical junction boxes 35. Cables 34 are flexibly mounted to accommodate travel of units 32 and 33. Junction boxes 35 are connected to suitable control and data acquisition subsystems such as described below with respect to FIG. 7.

Figure 7:
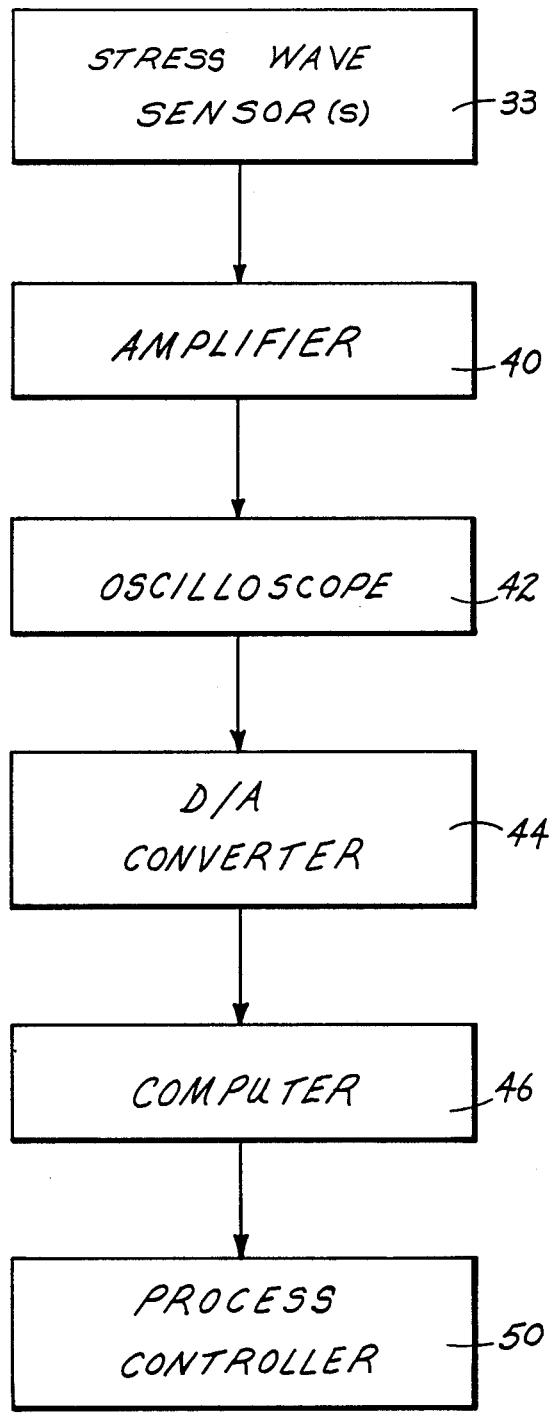
FIG. 7 is a schematic diagram showing a signal processing system advantageously employed with preferred embodiments of the invention.

FIG. 7 schematically shows a preferred sensor signal processing subsystem preferably employed with apparatus of this invention, such as testing machine 10. The output from sensors 33 are amplified by a suitable signal amplifier 40, well known in the art. The output from amplifier 40 is preferably connected to an oscilloscope 42 to provide visual indication of the output signals from sensors 33. Oscilloscope 42 can be a recording oscilloscope which preferably stores sensor output signal data in digital form. Conversion of the analog signal from sensors 33 can be accomplished by analog-to-digital (A/D) converter 44 which can be either integral or discrete from oscilloscope 42. The sensor signals can also be processed directed through A/D converter 44 without oscilloscope 42.

In an alternative form of the invention a sensor or sensor units are suitably amplified and the output signal recorded directly in analog form. This is advantageously done in the form of a small portable sensor amplifier unit and a small portable tape recorder or other equivalent data storage unit (both not shown). The signal amplifier and data storage units can be discrete or integrated. Data so stored can then be returned to the laboratory and analyzed on oscilloscope 42 and/or through A/D converter 44 and processed through subsequent analytical steps as explained below.

The digital output signal from A/D converter 44 is communicated to a suitable computer 46 which can be a general purpose computer provided with data acquisition software for storing the information processed from sensors 33. Computer 46 also is provided with software for analyzing the received sensor data along with additional informational inputs as will be described more fully below. The measured and predetermined information are useful for predicting mechanical properties of the composite material specimen 28.

Computer 46 can also be connected to a process controller 50 used to control manufacturing process control systems used in the production of panels 28. Testing machine 10 can thus be used to directly control manufacturing by defining optimum control ranges for maintaining the mechanical properties of end products within desired ranges.

The operation of testing machine 10 will now be described. Panel 28 is conveyed to testing machine 10 using any suitable conveying equipment or other means (not shown). The panel is fed horizontally across machine 10 by the rolling action of rollers 26. The position of panel 28 is stopped at a desired point and the rams 30 are extended to place stress wave producing unit 32 and sensing units 33 into contact with panel 28. Where noncontacting sensors are used there is no need for actual contact by sensors 33. Contact of units 32 and 33 helps to stabilize the panel during testing.

Testing is effectuated by actuating stress wave unit 32 to produce a freely moving or self propagating stress wave within panel 28. A variety of different stress wave modes of action may actually be induced by unit 32. Of principal interest is the production of longitudinal stress waves within specimen 28. The longitudinal stress waves radiate through the composite material panel at a velocity which is dependent upon the type of material used and the strength of the material, and the elastic properties of the material.

The inventors have discovered three factors which can be combined to reliably relate and predict mechanical strength and elastic properties of individual structural elements such as panel 28. These factors are: the square of the wave speed through the material; the density or specific gravity of the material; and the rate of attenuation of the wave energy as it passes through the composite material structural element.

It has been found that the strength in flexure or bending, the ultimate tensile strength, and the internal bonding strength can be reliably tested and predicted. It has also been found that the modulus of elasticity in bending and in tension can be reliably tested and predicted. Other mechanical strength and elastic properties may be predictable.

The prediction of the indicated and possibly other mechanical properties is based upon the relationship exprssed by Equation 1 below:

Equation 1 $P = a^D x (ATT)^y (C^2)^z$ where:
P = the mechanical property being predicted
a = is a coefficient specific to the system, materials, and structural elements employed
D = the density or specific gravity
ATT = the rate of attenuation of the stress wave intensity
C = the wave speed through the material
x, y and z = experimentally derived parameters specific to the system, materials, and structural elements used The attenuation rate (ATT) is typically defined as the average rate of attenuation of the stress wave. More specifically, it has been found represented as the average rate of particle velocity attenuation where velocity measurements are made of the particles forming the structural element. Attenuation in systems measuring wave dynamics by changed displacement and acceleration variations can also be used where appropriate interpretation is made in accordance with the physical theories of wave phenomenon.

The average rate of attenuation can advantageously be expressed as the percentage decline in particle maximum velocity per distance of travel through the composite material. The attenuation rate is measured during testing using the stress wave sensors 33 and the known distances between stress wave producing unit 32 and the stress wave sensors 33. Each sensor 33 thus indicates a different wave intensity which decreases with distance traveled through the material. The rate of decrease or attenuation varies in relationship to the strength of the structural element being tested. The attenuation rate cannot, however, be used alone to provide a reliable indication of the indicated mechanical properties. The other measured quantities of wave speed and material density also are not by themselves reliable indicators of the mechanical properties of entire structural elements made from composite materials.

Testing machine 10 records the time of sensing of the propagating stress waves at the three different sensors 33 using computer 46. The sensor geometry is known and the distance through which the stress wave propagates within the composite material is also known. From the known spacial geometry and measured times of sensing of the stress wave, it is possible to determine the wave speed C. The measured wave speed, C, and measured attenuation rate, ATT, are then expressed into Equation 1 along with predetermined values for a, x, y, z and D.

The density, D, is typically measured in advanced and preprogrammed into computer 46. Density is typically maintained within a sufficiently narrow range during manufacturing so that item-by-item specific measurements of density are not required. Where density varies significantly, adjustments must be made in conformance with Equation 1 to provide reliable prediction of mechanical properties.

The predetermined values for a, x, y, and z are preferably determined by testing a population of structural elements such as panel 28 and then destructively or otherwise determining the flexural, tensile, and internal bond breaking strengths using well known destructive testing methods and apparatuses. When Equation 1 is used to predict elastic properties of the structural element such as the elastic modulii in bending or tension, then it is necessary to establish such predetermined parameters experimentally using accepted methods of determining the static or dynamic modulii of elasticity, well known in the art. Experimental establishment of the predetermined parametric values for Equation 1 should be performed for each type or specific testing apparatus 10. The values for parametric parameters a, x, y, and z should also be experimentally established for each type of structural element being analyzed and for each composition of composite materials used in the structural element.

Experimental establishment of parameters a, x, y and z is advantageously accomplished using regression correlation techniques. In such techniques the measured strength or elasticity from experimental testing is correlated to the measured stress wave speed C, attenuation rate (ATT) and density D for the same specimens. A statistically significant number of specimens are used and an effective mathematical relationship is established which relates the destructive testing established values to the three measured variables of Equation 1. The regression technique correlates the experimental values and allows estimation of the predictive parameters a, x, y and z so that reliable prediction can be made of the mechanical properties using the measured varibles C, ATT and D.

Computer 46 preferably includes analytical software for automatically calculating wave speed (C) and attenuation (ATT). Predetermined experimentally derived parameters a, x, y and z are further coupled with information on the density or specific gravity so that a predicted value of flexural or tensile strength, bond strength, or flexural or tensile elastic modulii can be predicted.

The predicted mechanical properties obtained using testing apparatus 10 and the included signal and data processing equipment described, can also be used to adjust manufacturing process controls 50 to maintain product quality within a desired range. This application of the invention provides closed-loop feedback control of the manufacturing process for the composite material structural components being produced.

Figure 3:
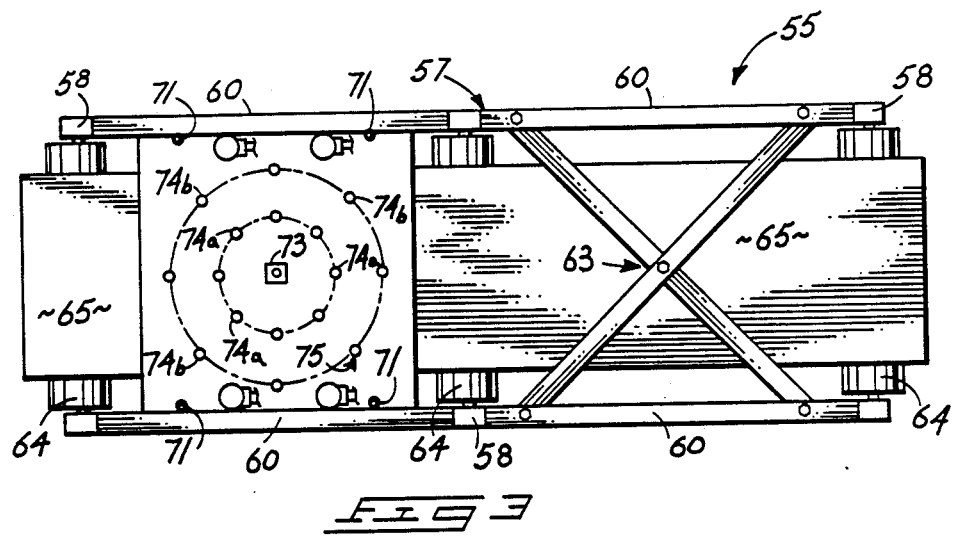
FIG. 3 is a top view of a second embodiment of the invention.
Figure 4:
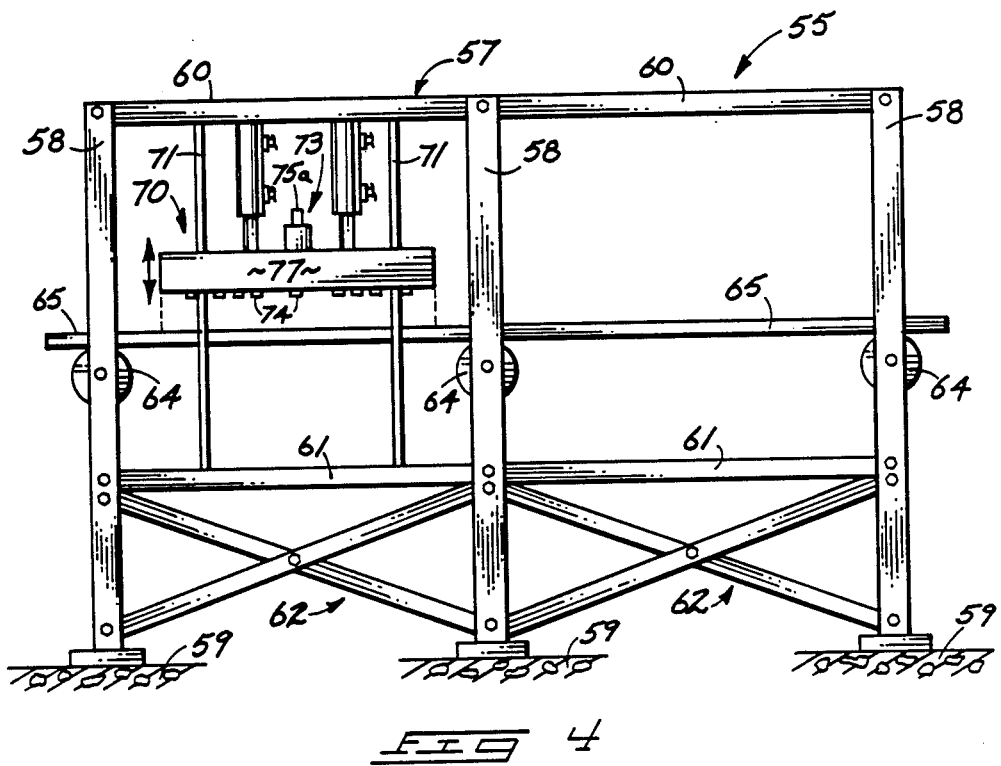
FIG. 4 is a side elevational view of the embodiment of FIG. 3.

Another embodiment of the invention is shown in FIGS. 3 and 4. The apparatus for nondestructively predicting mechanical properties 55 includes a structural framework 57. Framework 57 can be of any suitable design but is shown here with a plurality of columns 58 mountable upon a foundation 59. Upper and lower beams 60 and 61, respectively extend between columns 58 along both sides of framework 55. Cross-bracing 62 and top cross-bracing 63 are advantageously used to increase stability.

Framework 57 is adapted to rotatably support a plurality of panel support rollers 64. Rollers 64 are approximately horizontal to support a specimen panel 65 positioned horizontally thereon. Apparatus 55 is shown with three rollers, additional rollers are also clearly possible. Rollers 64 are preferably driven using any suitable means as described above with respect to rollers 26.

Testing machine 55 further includes a movable head assembly 70 with a head assembly platen 77. Head asembly 70 is adapted and mounted for slidable vertical motion using a plurality of guide rods 71 connected to framework 57 and extending through apertures formed in head assembly platen 77. A plurality of pneumatic or hydraulic rams 72 are advantageously used to power head assembly 7 upwardly into a retracted position and downwardly into an extended position. Rams 70 are provided with pressured fluid in the usual manner through hoses (partially shown). Piping, control valves and pumps are not shown, but are preferably automatically controlled using a central control system preferably run by a control computer or general computer 46 described above.

Head assembly 70 is provided with an impactor 73 mounted centrally upon platen 77. Impactor 73 uses any suitable type of controllable impact rod or hammer such as linear solenoid actuated rod 73a which strikes panel 65 to produce a propagating longitudinal stress wave therein. Other alternative stress wave inducing means can also be used.

Head assembly 70 further includes a plurality of stress wave sensor units 74 which are advantageously mounted in recveiving and mounting holes 75 formed in the head assembly platen 77. Sensor units 74 can be of a variety of types as explained above with respect to sensor units 33.

FIG. 3 shows that sensor units 74 are preferable arranged in two or more approximately concentric circular arrays centered approximately upon the impactor 73. Sensors of the inner circle, designated 74a, are advantageously at eight equal-angularly spaced positions. Sensors of the outer circle, designated 74b, are advantageously at eight equal-angular positions along the same radial lines extending from impactor 73 through sensors 74a. This arrangement allows a stress wave to be produced at a central location and radiate outwardly. The propagating wave is first sensed by sensors 74a and secondly sensed by sensors 74b. The two circles of radially aligned stress wave sensors detect the same portion of the propagating wave front thus improving accuracy.

Testing machine 55 further includes appropriate control and signal processing subsystems. The control system (not shown) can be of any suitable type and can be manual or preferably automatic and coordinated with related panel conveying equipment (not shown). The control system controls infeed, stationary support and outfeed of panels 65 by controlling rotation of rollers 64 or other panel propulsion means (not shown). The control system also controls head 70 to be raised during panel movement and lowered into contact or near contact with the panel during the test sequence. The control can also function automatically to actuate the stress wave producing unit 73.

The signal processing subsystems useful in testing machine 55 are preferably constructed as described above and shown with respect to FIG. 7. Other alternative signal and data processing arrangements are also clearly possible.

Testing machine 55 is operated by supplying panels 65 thereto preferably along a rolling conveyor system (not shown). Panels 65 can enter from either side. Testing can occur at two or more positions of panel 65 so that sufficiently complete testing and predictions can be accomplished for the entire panel. The specific size and arrangement of sensors 74 and the size and shape of the panel will govern whether multiple testing is necessary.

The panel or other specimen is properly positioned by rotating rollers 64 until the desired location of panel 65 is achieved. Thereafter the platen 77 is extended downwardly into contact, near contact, or as required by the specific impactor 73 and sensor units 74 employed. Impactor 73 is thereafter actuated to impact the panel at a central location to produce an outwardly radiating longitudinal stress wave. The radiating stress wave is sensed as to intensity and time of arrival by the inner and outer circle of sensors, 74a, and 74b, respectively. The wave propagation speed is determined, preferably via computer 46, using the detected time difference between receipt at the first or inner sensors 74a and receipt at the second or outer sensors 74b. The attenuation rate is ascertained from the decrease in wave intensity between first and second sensors along each radical line. Analysis of data is preferably performed with respect to the eight separate channels associated with the eight sets of first and second sensors lying along the radial lines centered upon impactor 73.

The multiple radial sensor sets have a further advantage in that effectively eight different data sets are obtained for providing good baseline information from which individual variations can be more accurately compared. The various channel and possile multiple measurements for each panel are preferably weighted and analyzed in computer 46 to achieve a measure for the panel as a whole. From this information, one or more predictions are made of the mechanical strength and/or elasticity values exhibited by the particular panel 65 being tested and analyzed. The analysis of test data is performed in conjunction with predetermined parametric values as discussed above with respect to Equation 1 and the variables included therein.

FIGS. 5 and 6 show a still further embodiment of the invention. Testing apparatus 80 includes a first rolling conveyor unit 81 and a second rolling conveyor unit 82. First and second rolling conveyor units 81 and 82 can be of any suitable type adapted to convey and support structural elements 84 being tested and analyzed. A variety of such conveyors are well known in the art.

A variety of composite material elements may be tested and analyzed using apparatus 85. The material shown in FIG. 6 is a bonded graphite fiber and epoxy composite having fibers 84a and matrix 84b.

A conductive element placing apparatus 85 is preferably positioned adjacent to first conveyor 81 and is used to attach or apply a suitable conductive element 86 across the upper surface of the bar shaped element 84. The conductive element applied to composite structural element 84 is advantageously an electrically conductive coating or paint which can be brushed or preferably spray painted across the element using a suitable moving spray head (not shown) forming a part of conductive element placing unit 85. Such coating application apparatuses are well known in the art. The conductive element placing apparatus 85 can also use fast setting adhesives or other means for attaching discrete pieces of conductive wire or other material to the surface of structural specimen 84.

Second unit 82 is adapted to receive, support, and convey specimens 84 using rollers 87 attached to a frame 92. Unit 82 is preferably interrupted at a central or midpoint region 93 to provide relatively close positioning of a magnet 88. The opposing poles of magnet 88 are positioned across the specimen adjacent the conductive element or coating line 86 so that any movement of the conductive element with respect to the magnetic field will produce an electromotive force (EMF) within conductive element 86. The well known relationships of Faraday's Law of Electromotive Force teaches that movement of a conductor across a magnetic field produces a voltage directly proportional to the velocity of the motion experienced by the conductive element relative to the magnetic field. Thus, when conductive element or line 86 moves in response to the dynamic motion of the underlying specimen during propagation of a stress wave, an electromotive force or voltage is produced directly indicative of the intensity of the stress wave.

FIG. 6 shows that magnet 88 can be specially adapted to allow access of two contacting electrodes 95 at opposite sides of specimen 84 and at the ends of conductive element 86. Contacting electrodes 95 are preferably mounted on linear throw solenoids 96 or other movable mechanical or electro-mechanical mounting apparatus for controllably contacting electrodes 95 to conductive element 86 during actual testing. The electrodes are accordingly retracted upwardly during movement of the specimen to allow free ingress and egress of specimens 84. Alternative movable contacting electrode configurations will be apparent to those of skill in the art.

The single magnet velocity sensor described allows repeated measurement of the same stress wave reflecting back and forth within bar 84. The attenuation and velocity of the longitudinal stress wave can thus be easily and economically measured with a high degree of accuracy at a multitude of points using only a single stress wave sensor.

Testing apparatus 80 also includes an impactor 89 which can be any suitable type such as a pivoting weight 89a which is controllably pivoted to strike the end of specimen 84. Weight 89a is preferably powered to automatically return into a raised position in order to allow free supply of new specimens 84 from first unit 81 to second unit 82. Apparatus 80 can further be provided with contact rams 90 or other means for fixing the position of specimens 84 relative to the conveyor unit 82 and magnet 88.

The testing and mechanical property predicting system 80 also advantageously employs a suitable signal and data processing subsystem such as described with respect to FIG. 7.

The testing and mechanical property predicting system 80 is advantageously used in the following manner. Specimens 84 are conveyed to first conveyor 81 which positions the specimen for disposition of conductive element 86 thereon. After the conductive element 86 is applied to specimen 84, the specimen is conveyed onwardly to second unit 82. Rams 90 fix the position of specimen 84 after conductive element 86 has been positioned within the magnetic field of magnet 88. Contacting electrodes 95 are then extended downwardly to complete an electrical circuit through element 86.

The specimen is then impacted by impactor 89 and the resulting stress wave propagates with specimen 84 and the wave intensity is measured in time as the stress wave passes repeatedly through the bar and the portions of the bar adjacent the conductive element 86.

The sensor signals are amplified and analyzed to determine the wave speed and particle velocity adjacent the conductive element. The attenuation rate is calculated from the decrease in the specimen's maximum particle velocity experienced during repeated passage of the reflected stress wave. The particle velocity is imparted to conductive element 86 via intimate contact therewith. Measured or predetermined values of density or specific gravity are used in combination with the experimentally predetermined parameters of Equation 1 to predict mechanical properties of the composite material structural element 84 as described above.

The apparatuses described herein are advantageously constructed using metallic and other suitable well known materials formed into the machinery described. Variations in the specific form are clearly possible within the scope of the invention. Electrical constituents are constructed using well known control, signal and data processing technology.

Methods according to this invention allow prediction of mechanical properties of a structural element made from non-homogenous composite materials. The methods and apparatus of the invention are useful with non-homogeneous composite materials such as plywood, wafferboard, oriented strand board, medium density fiberboard, hardboard, insulation board, particleboard, and other adhesively bonded composite material. The invention is also useful with epoxy-graphite composite, fiberglass reinforced composites and many other elongated fiber-matrix composites well known in the art.

The methods involve impacting or otherwise producing a moving stress wave within the specimen or portion of specimen being tested. The intensity and time of the stress wave is measured at a first point in time. The stress wave is allowed to traverse through at least a portion of the specimen. The stress wave is again measured at a second point in time to determine the speed of the stress wave and the amount by which the wave intensity has attenuated. The first and second points in time at which the stress wave is measured may be either at separate locations, as in testing machines 10 and 57, or at the same measurement location, such as in testing machine 80.

The data of wave speed and rate of stress wave attenuation is combined with measured or predetermined data defining the density of the specimen. Other predetermined experimentally derived parameters are used in Equation 1 to provide a predictive formula specific to the size, type, specimen composition, and measurement system used. This formula or other equivalent data relating mechanical properties of the specimens to values of the measured inputs of stress wave speed, attenuation, and density allow reliable indications or predictions of the mechanical properties without destructively testing the specimen.

The methods of this invention can be used to test a portion or all of the structural element. Testing and analysis of the structural element as a whole provides a more reliable indication of the mechanical performance potential of the element.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. An apparatus for automatically and nondestructively testing a panel made of composite materials to quantitatively predict mechanical properties of the panel, comprising:
   a frame;
   means for conveying the panel with respect to the frame to allow a panel to enter into and be removed from at least one test position;
   at least one testing head movably mounted to the frame for motion toward and from a panel when in a test position;
   at least one stress wave producing means for engagement with said panel to produce at least one self-propagating stress wave in the panel which originates from at least one stress wave originating position on said panel;
   a plurality of stress wave sensing means mounted to at least one of the testing heads; the plurality of stress wave sensing means serving to detect stress wave propagation speed and stress wave attenuation; the plurality of stress wave sensing means being positioned at a plurality of sensor positions which detect stress wave action in the panel at positions which are spaced from the stress wave originating position; at least two of said stress wave sensing means being spaced apart to detect stress waves which propagate through said panel along stress wave paths which are distinct from one another;
   means for automatically moving at least one testing head toward the panel when the panel is in the testing position and away from the panel when testing is completed;
   means for automatically interpreting test data produced by said stress wave sensing means to produce measures of stress wave speed and stress wave attenuation; said means for interpreting test data including means for storing experimentally derived predetermined parameters;
   Means for analyzing measured test data and the predetermined parameters to derive a predicted measure of the elastic or strength property being tested; and
   wherein the plurality of stress wave sensing means includes at least one stress wave sensing means spaced substantially across the panel from a stress wave originating position, and at least one stress wave sensing means spaced along a length direction of the panel which is different in direction than across said panel.

2. The apparatus of claim 1 wherein the plurality of stress wave sensing means further includes at least one stress wave sensing means which is spaced from the stress wave originating position through a thickness of the panel.

3. An apparatus for automatically and nondestructively testing a panel made of composite materials to quantitatively predict mechanical properties of the panel, comprising:
   a frame;
   means for conveying the panel with respect to the frame to allow a panel to enter into and be removed from at least one test position;
   at least one testing head movably mounted to the frame for motion toward and from a panel when in a test position;
   at least one stress wave producing means for engagement with said panel to produce at least one self-propagating stress wave in the panel which originates from at least one stress wave originating position on said panel;
   a plurality of stress wave sensing means mounted to at least one of the testing heads; the plurality of stress wave sensing means serving to detect stress wave propagation speed and stress wave attenuation; the pluraliity of stress wave sensing means being positioned at a plurality of sensor positions which detect stress wave action in the panel at positions which are spaced from the stress originating position; at least two of said stress wave sensing means being spaced apart to detect stress waves which propagate through said panel along stress wave paths which are distinct from one another;
   means for automatically moving at least one testing head toward the panel when the panel is in the testing position and away from the panel when testing is completed;

means for automatically interpreting test data produced by said stress wave sensing means to produce measures of stress wave speed and stress wave attenuation; said means for interpreting test data including means for storing experimentally derived predetermined parameters;

means for analyzing measured test data and the predetermined parameters to derive a predicted measure of the elastic or strength property being tested; and wherein there are a plurality of stress wave sensing means arranged in a radial arrangement from a stress wave producing means; said stress wave sensing means being related in groups which include at least a pair of stress wave sensing means arranged substantially along a radial line from the stress wave originating position outwardly.

4. An apparatus for automatically and nondestructively testing a panel made of composite materials to quantitatively predict mechanical properties of the panel, comprising:

a frame; 'means for conveying the panel with respect to the frame to allow a panel to enter into and be removed from at least one test position;

at least one testing head movably mounted to the frame for motion toward and from a panel when in a test position;

at least one stress wave producing means for engagement with said panel to produce at least one self-propagating stress wave in the panel which originates from at least one stress wave originating position on said panel;

a plurality of stress wave sensing means mounted to at least one testing head; the stress wave sensing means serving to detect stress wave propagation speed and stress wave attenuation; the stress wave sensing means being positioned at a plurality of sensor positions to allow detection of stress wave action in the panel at positions or times which are spaced from the stress wave originating position at the time of stress wave creation;

means for automatically moving at least one testing head toward the panel when the panel is in the testing position and away from the panel when testing is completed;

means for automatically interpreting test data produced by said stress wave sensing means to produce measures of stress wave speed and stress wave attenuation;

means for storing experimentally derived predetermined parameters which relate to measurements of stress wave speed and stress wave attenuation;

means for analyzing measured test data and the predetermined parameters to derive a predicted measure of the elastic or strength property being tested; and wherein the plurality of stress wave sensing means include at least one stress wave sensing means spaced substantially across the panel from a stress wave originating position, and at least one stress wave sensing means spaced along a length direction of the panel which is different in direction than across said panel.

5. An apparatus for automatically and nondestructively testing a panel made of composite materials to quantitatively predict mechanical properties of the panel, comprising:

a frame;

means for conveying the panel with respect to the frame to allow a panel to enter into and be removed from at least one test position;

at least one testing head movably mounted to the frame for motion toward and from a panel when in a test position;

at least one stress wave producing means for engagement with said panel to produce at least one self-propagating stress wave in the panel which originates from at least one stress wave originating position on said panel;

a plurality of stress wave sensing means mounted to at least one testing head; the stress wave sensing means serving to detect stress wave propagation speed and stress wave attenuation; the stress wave sensing means being positioned at a plurality of sensor positions to allow detection of stress wave action in the panel at positions or times which are spaced from the stress wave originating position at the time of stress wave creation;

means for automatically moving at least one testing head toward the panel when the panel is in the testing position and away from the panel when testing is completed;

means for automatically interpreting test data produced by said stress wave sensing means to produce measure of stress wave speed and stress wave attenuation;

means for storing experimentally derived predetermined parameters which relate to measurements of stress wave speed and stress wave attenuation;

means for analyzing measured test data and the predetermined parameters to derive a predicted measure of the elastic or strength property being tested; and wherein the plurality of stress wave sensing means further includes at least one stress wave sensing means which is spaced from the stress wave originating position through a thickness of the panel.

6. An apparatus for automatically and nondestructively testing a panel made of composite materials to quantitatively predict mechanical properties of the panel, comprising:

a frame;

means for conveying the panel with respect to the frame to allow a panel to enter into and be removed from at least one test position;

at least one testing head movably mounted to the frame for motion toward and from a panel when in a test position;

at least one stress wave producing means for engagement with said panel to produce at least one self-propagating stress wave in the panel which originates from at least one stress wave originating position on said panel;

a plurality of stress wave sensing means mounted to at least one testing head; the stress wave sensing means serving to detect stress wave propagation speed and stress wave attenuation; the stress wave sensing means being positioned at a plurality of sensor positions to allow detection of stress wave action in the panel at positions or times which are spaced from the stress wave originating position at the time of stress wave creation;

means for automatically moving at least one testing head toward the panel when the panel is in the testing position and away from the panel when testing is completed;

means for automatically interpreting test data produced by said stress wave sensing means to produce measures of stress wave speed and stress wave attenuation;

means for storing experimentally derived predetermined parameters which relate to measurements of stress wave speed and stress wave attenuation;

means for analyzing measured test data and the predetermined parameters to derive a predicted measure of the elastic or strength property being tested; and wherein there are a plurality of stress wave sensing means arranged in a radial arrangement from a stress wave producing means; said stress wave sensing means being related in groups which include at least a pair of stress wave sensing means arranged substantially along a radial line from the stress wave originating position outwardly.

* * * * *